United States Patent [19]

Adger et al.

[11] Patent Number: 5,811,558

[45] Date of Patent: Sep. 22, 1998

[54] PROCESS FOR THE RESOLUTION OF ETODOLAC USING GLUCAMINE DERIVATIVES

[75] Inventors: Brian Michael Adger; Ulrich Conrad Dyer; Martin Woods; John Francis Paul Andrews; Helen Frances Baker, all of Cambridge, United Kingdom

[73] Assignee: Chiroscience Limited, United Kingdom

[21] Appl. No.: 727,503

[22] PCT Filed: Apr. 11, 1995

[86] PCT No.: PCT/GB95/00857

§ 371 Date: Dec. 6, 1996

§ 102(e) Date: Dec. 6, 1996

[87] PCT Pub. No.: WO95/27713

PCT Pub. Date: Oct. 19, 1995

[30] Foreign Application Priority Data

Apr. 12, 1994 [GB] United Kingdom .................... 9407225
Jan. 25, 1995 [GB] United Kingdom .................... 9501455

[51] Int. Cl.$^6$ ................................................. C07D 209/14

[52] U.S. Cl. .............................................................. 548/427
[58] Field of Search .............................................. 548/427

[56] References Cited

U.S. PATENT DOCUMENTS 4,748,174  5/1988  Veronesi ................................ 514/226.5

OTHER PUBLICATIONS

Demerson et al. J. Med. Chem. vol. 26, pp. 1778–1780 1983.

*Primary Examiner*—Deborah C. Lambkin
*Assistant Examiner*—Ebenezer O. Sackey
*Attorney, Agent, or Firm*—Saliwanchik, Lloyd & Saliwanchik

[57] ABSTRACT

The subject invention pertains to a process for the resolution of etodolac comprising the use of the resolving agent glucamine or a N-($C_{1-4}$ alkyl)-glucamine. The subject invention also concerns a process for converting a single enantiomer of etodolac into the racemate. The method comprises forming all ester of the carboxylate function of the enantiomer and treating with an acid or base.

6 Claims, 2 Drawing Sheets

PROCESS FOR THE RESOLUTION OF ETODOLAC USING GLUCAMINE DERIVATIVES

This application is a 371 of PCT/GB 95/00857 filed on Apr. 11, 1995.

FIELD OF THE INVENTION

This invention relates to etodolac, and in particular to novel enantiomeric salts thereof, a process for making those salts, and their use in the manufacture of medicaments.

BACKGROUND OF THE INVENTION

Etodolac is a chiral compound. It is a non-steroidal analgesic and anti-inflammatory agent which is marketed in racemic form. Its analgesic properties and preparation are described in US-A-3843681 and sustained-release formulations containing it are described in EP-A-0309157. The existence of its meglumine and glucamine acid addition salts is disclosed in US-A-4748174, although the preparation and properties of these salts is not.

It has been found that the required biological activity of etodolac generally resides in only one of its enantiomers, for instance as described by Demerson et al, J. Med. Chem., (1983) 26:1778. Consequently, there is a need for a process to produce that single enantiomer. An existing resolution procedure is disclosed in US-A-4520203, and involves crystallisation of a single diastereoisomeric salt formed with etodolac and the alkaloidal base cinchonine. However, a disadvantage with this process is that the resolving agent used is both expensive and toxic.

Another resolution procedure is disclosed in US-A-4515961 and resolves etodolac as a conglomerate from a solution of the racemate.

SUMMARY OF THE INVENTION

According to a first aspect of the present invention, a compound that is a glucamine or an N-($C_{1-4}$ alkyl)- glucamine salt of (S)-etodolac, preferably the meglumine salt of (S)-etodolac. The meglumine salt has a surprisingly short $t_{max}$, thus making it particularly suitable for rapid-onset analgesic effect. In addition, surprisingly, the use of the meglumine salt of (S)-etodolac leads to a reduction in variation in plasma concentrations from subject to subject, and also to a more complete absorption, indicated by an increase in AUC, compared to the racemate. In summary, the meglumine salt produces a significantly more consistent blood level of the (S) enantiomer than does the racemate.

According to a second aspect of the present invention, use of a water soluble (S)-etodolac salt is in the manufacture of a medicament for use in rapid-onset analgesia, e.g. in treating acute pain.

According to a third aspect of the present invention, use of a water-soluble salt of (S)-etodolac is in the manufacture of a medicament for use in managing chronic pain, eg arthritis.

The $t_{1/2}$, values for racemic etodolac and (R)-etodolac are substantially eguivalent while the corresponding value for (S)-etodolac is markedly lower. This, in addition to the reduction in variation in plasma concentrations described above, supports the utility of (S)-etodolac in sustained-release formulations.

According to a fourth aspect of the present invention, a sustained-release formulation comprises (S)-etodolac, or a water-soluble salt thereof, preferably the meglumine salt of (S)-etodolac.

According to a fifth aspect of the present invention, a process for the resolution of etodolac comprises using as the resolving agent glucamine or an N-($C_{1-4}$ alkyl) -glucamine. Resolving agents of this type are cheap and readily available, and are also non-toxic which means that they can be retained in the final drug formulation, if so desired, as they form pharmaceutically-acceptable salts.

According to a sixth aspect of the present invention, a process for converting a single enantiomer of etodolac into the racemate comprises forming an ester of the carboxylate function of that enantiomer and treating with acid or with base, preferably with acid. Consequently, the above process for resolving etodolac, or indeed any other such process, can be made economically viable by recycling the unwanted enantiomer in this way.

DESCRIPTION OF THE INVENTION

The novel enantiomeric salts of the present invention are substantially enantiopure. Preferably they are in at least 80% ee, more preferably at least 90% ee, and most preferably at least 97% ee or even 100% ee, with respect to the (R) enantiomer.

When the meglumine salt, for example, of (S)-etodolac is dosed orally, it appears in the plasma very rapidly. Indeed, its plasma profile is more like an intravenous drug than an oral drug. It is implicit in the mechanism of action of the drug that a minimum plasma concentration has to be attained before the drug takes effect. The faster that minimum concentration is attained, the quicker the analgesic effect. This can be particularly beneficial in some pain indications where it is generally clinically accepted that the faster the pain is relieved, the lower the total amount of pain. This, together with the reduction in variability of plasma concentrations observed with the meglumine salt as compared to the racemate, allows the administration of smaller doses of etodolac than have formerly been used, with the certainty of achieving the plasma concentration required for the drug's efficacy.

The enantiomer equivalent dose of the meglumine salt as compared to 200 mg racemate is in the range 10 to 100 mg, and is typically in the range 20 to 50 mg.

Summarising the above, the present invention has the potential to reduce the amount of drug that is necessary for the treatment of pain, and this could lead to reduced side effects, as gastrointestinal side effects, for example, are also related to the (S) enantiomer.

These properties render the water soluble salts of (S)-etodolac, and in particular the meglumine salt thereof, suitable for rapid onset analgesia, for instance in indications such as acute pain, post-operative pain, trauma, breakthrough pain (from chronic cancer pain), labour, and also in accident and emergency.

Surprisingly, it has also been found that, following oral dosing with the racemate, plasma concentrations of (R)-etodolac are about 10 times higher than that of (S)-etodolac. This is the result of the differences in $t_{1/2}$ of the two enantiomers: $t_{1/2}$ for (S)-etodolac and for (R)-etodolac is about 2 hours and about 7 hours, respectively. Through use of a sustained, or controlled, -release formulation comprising (S)-etodolac, it is possible to achieve plasma concentrations of this active enantiomer which are above the minimum level required for its efficacy throughout the duration of the dosing period. This is a considerable improvement on sustained release-formulations comprising racemic etodolac, as with these there may be intervals in the dosing period where the concentration of (S)-etodolac drops below the minimum required level.

Sustained-release formulations are particularly suitable for the management of chronic pain, for example in treating arthritis. Suitable sustained-release formulations are described in EP-A-0309157.

Conventional, or immediate, release formulations may also be used to administer (S)-etodolac, or a salt thereof, particularly for rapid-onset analgesia. Examples of suitable formulations include oral formulations, eg tablets, capsules, solutions, suspensions, gels etc; nasal sprays; inhalers; rectal systems, e.g. suppositories, enemas, foams etc; injectables, e.g. for intravenous, subcutaneous, intramuscular, intra-synovial use etc; and topical forms, e.g. creams, ointments, gels and patches.

Irrespective of the kind of formulation used, the formulation can include a number of excipients in addition to the drug. Examples of such excipients, for use in oral tablets and capsules in particular, include fillers or bulking agents such as lactose and cellulose; binders such as polyvinylpyrrolidone; disintegrants such as starch or Explotab®; lubricants such as magnesium stearate; coatings such as sugar-based materials, or films such as hydroxymethyl cellulose; flavours and/or sweeteners such as phenylalanine and saccharin; and colourings such as titanium dioxide or iron oxides. Such excipients are typically used in their standard amounts.

(S)-etodolac or a salt thereof, can be the sole pharmaceutically-active agent in a drug formulation. Alternatively, it can be combined with other pharmaceutically-active agents, such as a gastroprotectant eg misoprostol or cyclodextrins; analgesics, e.g. opiates or paracetamol; other NSAIDs; adjuvants, e.g. caffeine; or cough-cold remedies, e.g. anti-histamines or sedatives.

It is envisaged that in addition to being useful in rapid onset analgesia and in managing chronic pain, (S)-etodolac, or a salt thereof, may have a number of other medical indications, for instance in inhibiting joint alkylosis; in inhibiting bone resorption; and in treating gout.

The novel enantiomeric salts of the invention can be prepared by resolving etodolac as outlined in Scheme 1 below where the resolving agent is, for example, meglumine (N-methyl-(D)-glucamine). In principle either the (S) or (R) enantiomer of etodolac in the salt form can be obtained depending upon the conditions used, and the free acid isolated if so desired.

The procedure is especially expedient since:
(i) racemic etodolac is readily available through methods established on an industrial scale; and
(ii) unlike cinchonine, (−)-meglumine is a pharmaceutically-acceptable counterion for a drug salt-form, so that cleavage of the salt after resolution is not obligatory, thereby potentially reducing the number of process steps to a suitable drug formulation.

Suitable solvents for the resolution include any available ethers, esters, ketones, amides, alcohols, nitriles, water and mixtures thereof. It is necessary that the starting material dissolves in the solvent at ambient or elevated temperature, and that precipitation of the respective etodolac salt is possible therefrom. Preferred solvents are polar solvents such as ketones, alcohols, nitriles, amides and water. Most preferred solvents are alcohols, particularly alkanols, especially ethanol and isopropanol.

The concentration of racemic etodolac in the solvent depends upon the nature of the solvent and the temperature of crystallisation to be used. Preferably, it will be in the range 0.01 to 2.5 g/ml, and most preferably between 0.1 to 0.2 g/ml.

The temperature of crystallisation depends upon the concentration of the drug and the nature of the solvent. Preferably it is in the range 0 to 70° C., and most preferably 35 to 55° C. using ethanol or isopropanol at a concentration of 0.15 g/ml based on racemic etodolac. Crystallisation can be facilitated by seeding, preferably using crystals that are significantly enriched in one enantiomer, and more preferably using 100% ee of the desired enantiomer.

It has also been found that enantiomeric esters of etodolac can be racemised effectively upon treatment with a catalytic amount of an acid or acid resin in an organic solvent. This is wholly surprising because heating etodolac free acid under acidic conditions leads to its decomposition, as described by Lee et al, J. Pharm. Sci., (1988) 77(1):81–86. Suitable acids are preferably inexpensive acids such as hydrochloric acid, sulphonic acid resin or sulphuric acid. Most preferably the acid is concentrated sulphuric acid. Suitable organic solvents are ethers, esters, ketones, amides, alcohols, nitriles and mixtures thereof, preferably alcohols, most preferably an alcohol corresponding to the alkoxy group of the respective ester.

Alternatively, the above racemisation can be carried out by treating an enantiomeric ester with a catalytic amount of base in an organic solvent such as those described above. Suitable bases are any non-hydroxide bases capable of effecting the required elimination and re-addition reactions to attain the racemate.

The esters can be cleaved by saponification to liberate racemic etodolac. Consequently, in a preferred embodiment of the present invention, after resolving etodolac the unwanted enantiomer is recycled using the above-described racemisation process.

This particular transformation of an enantiomer into the racemate has the benefit of using cheap and readily available materials, and also that the saponification step can be combined with an industrial process for the synthesis of the racemate where the immediate precursor of etodolac is an ester. The esterification, racemisation and saponification steps are preferably combined, for example in the same reaction vessel.

The resolution process of the invention is capable of preparing (S)-etodolac, or a salt thereof, that is substantially enantiopure. Preferably, (S)-etodolac is produced in an enantiomeric excess of at least 80%, more preferably at least 90%, and most preferably at least 97% or even 100%, with respect to (R)-etodolac. Recrystallisation, for example from an alcohol such as isopropanol, can further increase this purity where desired.

The present invention is now further illustrated by the following examples, in which FIGS. 1 and 2 below are referred to.

EXAMPLES

Example 1: Resolution of Etodolac

Racemic etodolac (1148 g) and N-methylglucamine (780.8 g) in ethanol (6.4 litres) were heated to 70° C. with stirring. The solution was cooled to 45° C. and then seeded with crystals of 100% ee (R)-etodolac meglumine salt and the mixture allowed to crystallise for 5 hours. The solid was filtered to provide (R)-etodolac (610 g, 86.4% ee) which could be recycled to racemic etodolac following the procedure in Example 2 below.

The mother liquors were heated to 50° C. to dissolve solids, cooled to 40° C. and then seeded with crystals of 100% ee (S)-etodolac. The mixture was stirred for 2 hours at 35° C., and was then filtered and washed with ethanol to provide (S)-etodolac meglumine salt (610 g, 80% ee). The material could be further enriched in (S) enantiomer by recrystallisation from ethanol or isopropanol.

Example 2: Racemisation of Etodolac (R)-Etodolac (1.0 g) is dissolved in methanol (20 ml) and treated with concentrated sulphuric acid (0.06 equiv). The mixture is heated under reflux for 3 days then cooled to ambient temperature. The racemic ester is deposited as a white crystalline solid and collected by filtration (60% yield). The racemic ester is treated with aqueous sodium hydroxide to effect hydrolysis, then acidified with acetic acid to pH 4 to give racemic etodolac as an off-white microcrystalline powder.

Example 3

An open randomised two way crossover study was conducted on a group of 13 healthy male volunteers to investigate the pharmacokinetics of the meglumine salt of (S)-etodolac and racemic etodolac (Lodine®); 11 volunteers received both treatments. Doses used were 168 g of the meglumine salt (equivalent to 100 mg of the free acid) and 200 mg of racemic etodolac. Blood samples were taken regularly.

Etodolac had no affect on vital signs, ECGs, physical examinations or on any clinical laboratory assessments, including serum biochemistry, haematology and urinalysis, when administered in either form.

The results of the pharmacokinetic study are shown in Table 1 and in FIGS. 1 and 2 below.

Figure 1:
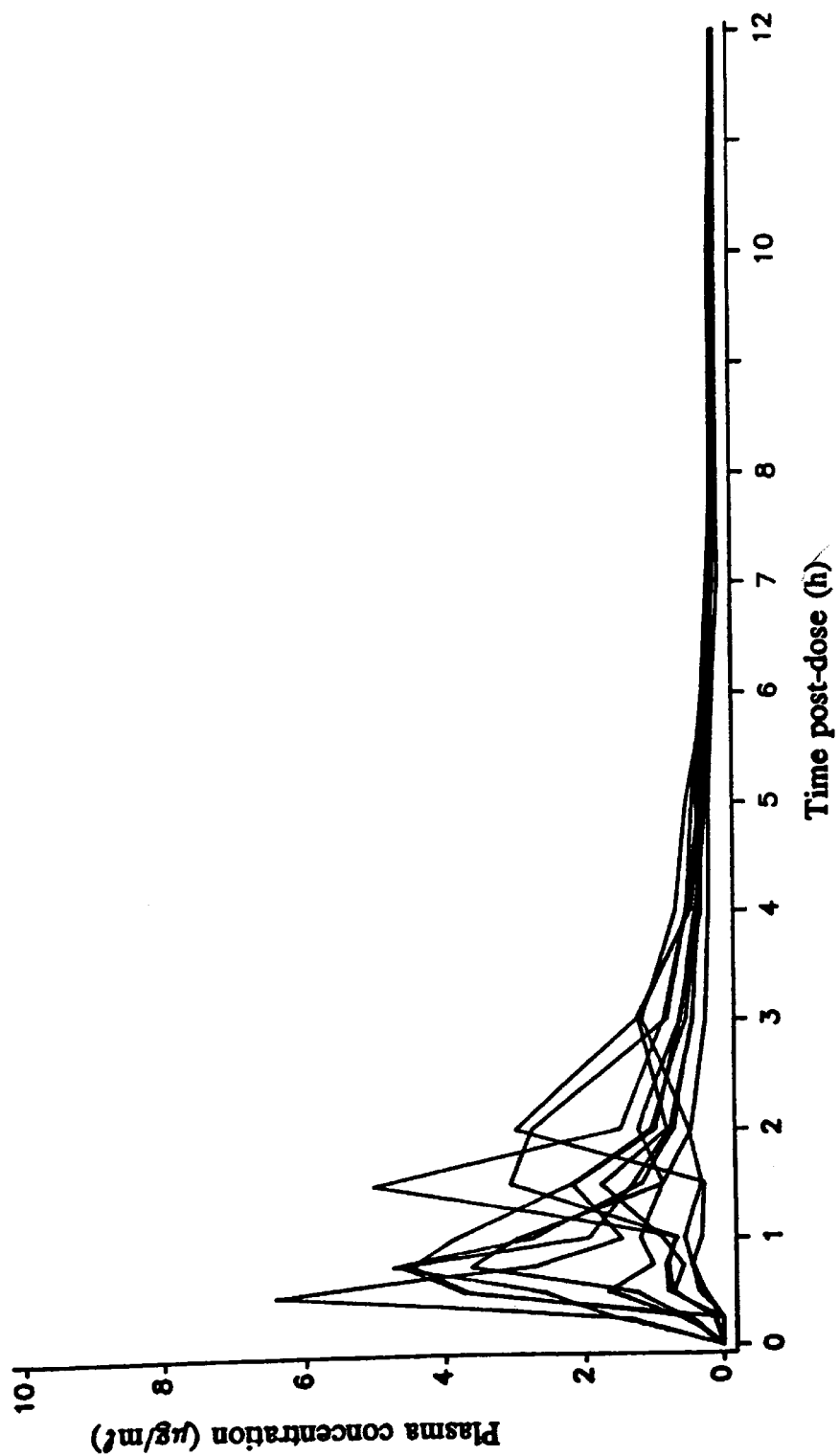
FIG. 1 is a graph of plasma concentration ($\mu$g/ml) of the (S)enantiomer for all volunteers receiving a single oral dose of 200 mg of racemic etodolac.
Figure 2:
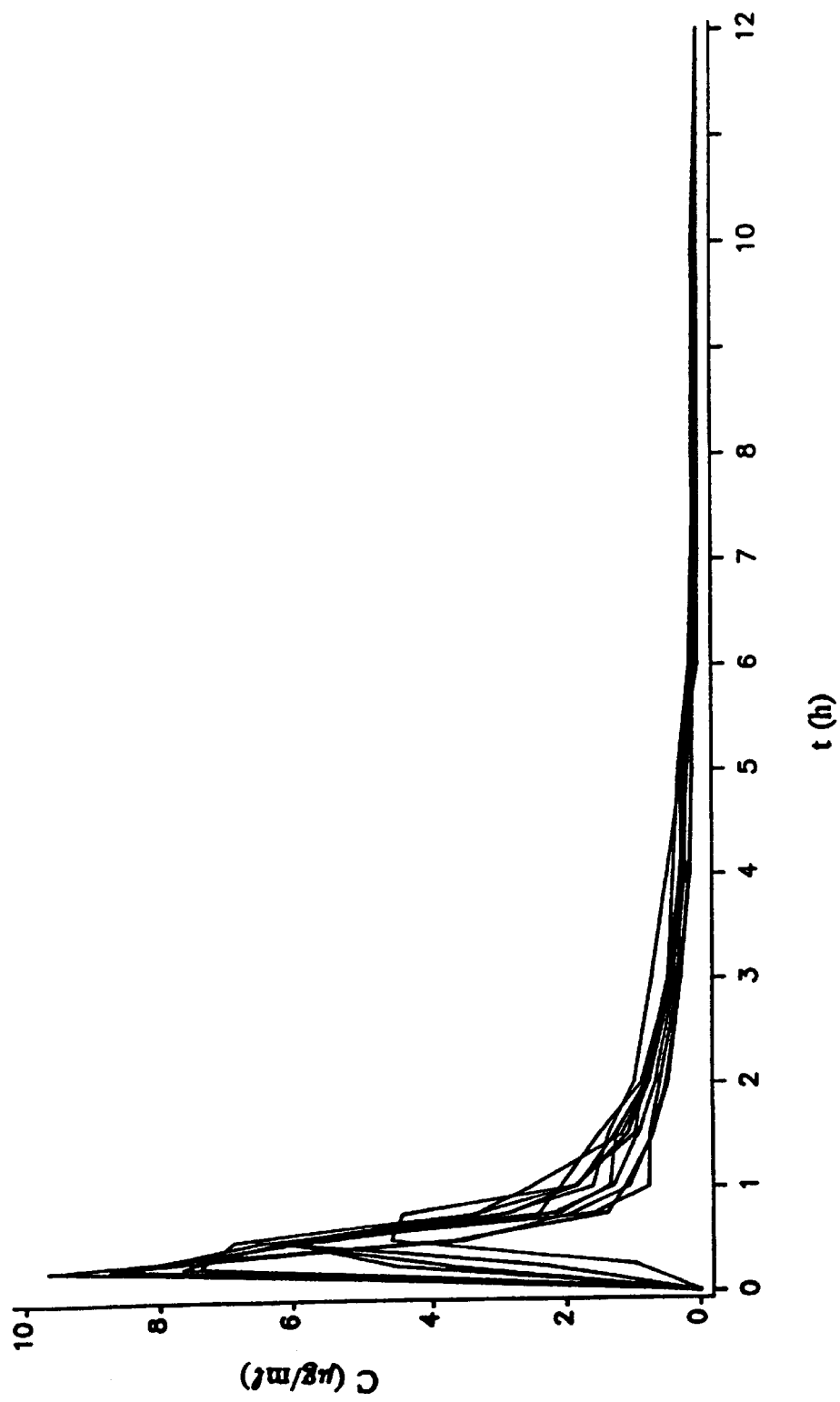
FIG. 2 is a graph of plasma concentration ($\mu$/ml) of the (S) enantiomer for all volunteers receiving a single oral dose of 168 mg of the meglumine salt of (S)-etodolac (100 mg free acid equivalent).

Comparing FIGS. 1 and 2, the peak plasma concentrations in FIG. 2 are significantly higher and occur earlier than the peak concentration in FIG. 1. This demonstrates the surprisingly rapid absorption of the (S) enantiomer when in the form of the meglumine salt compared to the racemate. In addition, the spread of the blood level concentrations in FIG. 2 is significantly narrower than that in FIG. 1, demonstrating a lower inter-volunteer variability in the plasma concentrations following administration of the meglumine salt compared to the racemate.

TABLE 1

|  | AUC ($\mu$g · h/ml) | $C_{max}$ (mg/ml) | $t_{max}$ (min) | t½ (min) |
|---|---|---|---|---|
| Meglumine salt of (S)-etodolac | 6.5* | 7.5* | 20* | 2.5 |
| Lodine ® | | | | |
| (S) enantiomer | 5.4 | 3.6 | 74 | 2 |
| (R) enantiomer | 85 | 16.9 | 104 | 7.2** |
| total etodolac | 90 | 20.2 | 100 | 7.14** |

*$p < 0.05$ compared to (S) enantiomer in Lodine ®
**$p < 0.05$ compared to (S) enantiomer in Lodine ® and in the form of the meglumine salt

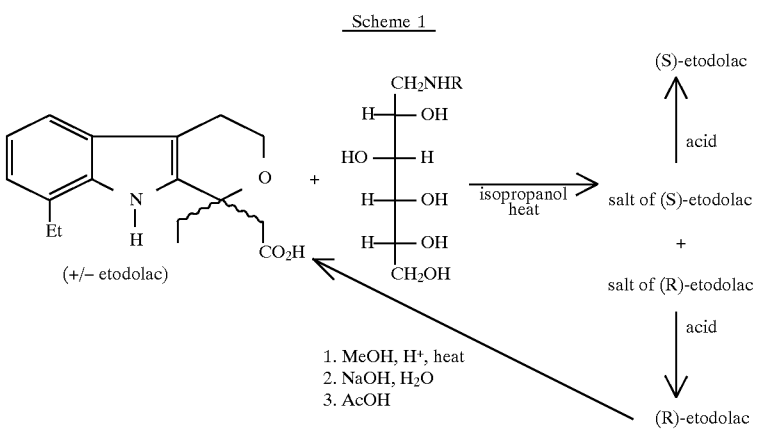

Scheme 1

We claim:

1. A process for preparing a glucamine or an N-($C_{1-4}$ alkyl glucainine salt of (S)-etodolac, comprising resolving racemic etodolac using, as the resolving agent, glucamine or an N-($C_{1-4}$ alkyl)-glucamine.

2. The process according to claim 1, wherein the resolving agent is meglumine.

3. The process according to claim 1, which is conducted in an alcoholic solvent.

4. The process according to any of claim 1, which additionally comprises racemising the unwanted enantiomer by formation of an ester of the carboxylate function and then acid treatment.

5. A process for converting a single enantiomer of etodolac into the racemate, which comprises forming an ester of the carboxylate function of that enantiomer and treating with acid or with base.

6. The process according to claim 5, wherein the ester is treated with acid.

* * * * *

UNITED STATES PATENT AND TRADEMARK OFFICE
CERTIFICATE OF CORRECTION

PATENT NO. : 5,811,558

DATED : September 22, 1998

INVENTOR(S) : Adger *et al.*

It is certified that error appears in the above-identified patent and that said Letters Patent is hereby corrected as shown below:

Column 6, line 49-50 (Claim 1): "N-($C_{1-4}$ alkyl glucainine" should read --N-($C_{1-4}$ alkyl) glucamine--.

Column 6, line 57 (Claim 4): "according to any of claim 1" should read --according to claim 1--.

Signed and Sealed this

Second Day of February, 1999

Attest:

Attesting Officer

*Acting Commissioner of Patents and Trademarks*